(12) United States Patent
Obeng

(10) Patent No.: US 12,276,607 B2
(45) Date of Patent: Apr. 15, 2025

(54) SYSTEM AND METHOD FOR MONITORING ULTRAVIOLET RADIATION BIOREMEDIATION

(71) Applicant: Government of the United States of America, as represented by the Secretary of Commerce, Gaithersburg, MD (US)

(72) Inventor: Yaw Samuel Obeng, Frederick, MD (US)

(73) Assignee: GOVERNMENT OF THE UNITED STATES OF AMERICA, AS REPRESENTED BY THE SECRETARY OF COMMERCE, Gaithersburg, MD (US)

( * ) Notice: Subject to any disclaimer, the term of this patent is extended or adjusted under 35 U.S.C. 154(b) by 817 days.

(21) Appl. No.: 17/520,116

(22) Filed: Nov. 5, 2021

(65) Prior Publication Data

US 2022/0136967 A1 May 5, 2022

Related U.S. Application Data (60) Provisional application No. 63/110,150, filed on Nov. 5, 2020.

(51) Int. Cl.
*G01N 21/47* (2006.01)
*A61L 2/28* (2006.01)
(Continued)

(52) U.S. Cl.
CPC ............ *G01N 21/47* (2013.01); *A61L 2/28* (2013.01); *C12Q 1/689* (2013.01); *G01N 22/00* (2013.01)

(58) Field of Classification Search
CPC .......... G01N 21/47; G01N 22/00; A61L 2/28; C12Q 1/689
See application file for complete search history.

(56) References Cited

U.S. PATENT DOCUMENTS

2010/0082084 A1* 4/2010 Brannan ............... A61B 18/18
607/101
2010/0328142 A1* 12/2010 Zoughi ................ H01Q 21/064
342/179

(Continued)

OTHER PUBLICATIONS

Goh, J.K., et al., "Non-Invasive Microwave Sensor for the Detection of Lactic Acid in Cerebrospinal Fluid (CSF)", Journal of Physics: Conference Series, 2011, p. 012017, vol. 307.

(Continued)

*Primary Examiner* — Nicole M Ippolito
(74) *Attorney, Agent, or Firm* — Office of Chief Counsel for National Institute of Standards and Technology (57) ABSTRACT

Embodiments of the present invention relate to a system and method for detecting biological material on surfaces after decontamination with UV-C and with high sensitivity and having low detection limits while providing rapid and efficient response to accommodate high turnover. Embodiments of the present invention monitor the disinfection process by detecting changes in the electrical properties of surface-confined biological thin films photodegraded with UV-C radiation using microwaves (MW). MW sensing provides noninvasive, real-time detection of the electromagnetic properties of biological materials via concentrated electromagnetic fields, for which advantages include wide bandwidth, small size, and cost-effective fabrication.

20 Claims, 7 Drawing Sheets

(51) Int. Cl.
*C12Q 1/689* (2018.01)
*G01N 22/00* (2006.01)

(56) References Cited

U.S. PATENT DOCUMENTS

| | | | |
|---|---|---|---|
| 2017/0199134 A1* | 7/2017 | LoVetri | A61B 5/0536 |
| 2019/0142513 A1* | 5/2019 | Witte | A61N 1/403 607/101 |
| 2021/0177310 A1* | 6/2021 | Nakamura | G01N 21/3581 |

OTHER PUBLICATIONS

Blakey, R.T., "Development of Dielectric Spectroscopic Resonant Sensors for Biomedical and Industrial Applications", Ph.D Thesis for Liverpool John Moores University, 2014, p. 1-194.

Blakey, R.T., et al., "Utilisation of an Embedded Resonant Structure to Differentiate Lipomyces Yeast Cultures based upon Lipid Content and Concentration", IEEE: 2013 Seventh International Conference on Sensing Technology, 2013, p. 963-967.

Xu, Y., et al., "A Review of Imdedance Measurement of Whole Cells", Biosensors and Bioelectronics, 2016, p. 824-836, vol. 77.

Mansoorifar, A., et al., "Electrical Impedance Measurements of Biological Cells in Response to External Stimuli", Analytical Chemistry, 2018, p. 4320-4327, vol. 90.

Santonicola, M.G., et al., "Nanomaterial-Based Biosensors for a Real-Time Detection of Biological Damage by UV Light", IEEE, 2015, p. 4391-4394.

Blakey, R.T., et al., "A Fluidic Cell Embedded Electromagnetic Wave Sensor for Online Indication of Neurological Impairment during Surgical Procedures", Journal of Physics: Conference Series, 2013, p. 012024, vol. 450.

Blakey, R.T., et al., "Microwave Dielectric Spectroscopy—A Versatile Methodology for Online, Non-Destructive Food Analysis, Monitoring and Process Control", Engineering in Agriculture, Enviroment and Food, 2016, p. 264-273.

* cited by examiner

100

```
┌─────────────────────────────────────┐
│   PREPARE SUBSTRATE COMPOSED OF     │ 102
│       BIOLOGICAL MATERIALS          │
└─────────────────────────────────────┘
                  │
                  ▼
┌─────────────────────────────────────┐
│   POSITION SUBSTRATE-BIOLOGICAL     │
│   MATERIAL ON A GROUND-SIGNAL-      │ 104
│   GROUND COPLANAR WAVEGUIDE         │
└─────────────────────────────────────┘
                  │
                  ▼
┌─────────────────────────────────────┐
│   IRRADAIATE BIOLOGICAL MATERIAL    │ 106
│        USING UV-C RADIATION         │
└─────────────────────────────────────┘
                  │
                  ▼
┌─────────────────────────────────────┐
│   MONITOR MICROWAVE SCATTERING      │
│   USING A VECTOR NETWORK            │ 108
│            ANALYZER                 │
└─────────────────────────────────────┘
                  │
                  ▼
┌─────────────────────────────────────┐
│  COLLECT S-PARAMETERS OF DEVICE     │ 110
│         UNDER TEST (DUT)            │
└─────────────────────────────────────┘
                  │
                  ▼
┌─────────────────────────────────────┐
│     EXTRACT ELECTRICAL              │
│  CHARACTERISTICS FROM S-            │ 112
│    PARAMETERS OF THE DUT            │
└─────────────────────────────────────┘
```

SYSTEM AND METHOD FOR MONITORING ULTRAVIOLET RADIATION BIOREMEDIATION

CROSS-REFERENCE TO RELATED APPLICATION

This application claims the benefit of priority from U.S. Provisional Patent Application Ser. No. 63/110,150, filed on Nov. 5, 2020, the disclosure of which is incorporated herein by reference.

STATEMENT REGARDING FEDERAL RIGHTS

The invention described herein was made with United States Government support from the National Institute of Standards and Technology (NIST), an agency of the United States Department of Commerce. The United States Government has certain rights in the invention.

FIELD OF THE INVENTION

The present invention relates generally to monitoring ultraviolet radiation disinfection performance, and more particularly, to a system and method for monitoring the efficacy of ultraviolet radiation bioremediation.

BACKGROUND OF THE INVENTION

Ultraviolet-C (UV-C) irradiation decontaminates surfaces by creating photodimeric lesions in DNA and RNA that disrupt reverse transcription/transcription, translation and replication to inactivate viruses, bacteria and spores. The germicidal efficacy is frequently quantified with basic microbiological techniques. After a specimen standard is exposed to a dose of UV-C, the surviving number of colony-forming units (CFUs) is determined from the growth plate counts quantified days after exposure. Limited best practices for minimizing biological and technical error in CFU counting are available. Typical decontamination indicators include (i) biological indicators that directly determine survivability of the most resistant microorganisms (e.g., *Geobacillus stearothermophilus*), (ii) mechanical indicators (gauges and digital displays), and (iii) chemical indicators (e.g., autoclave tape) which indicate that the sterilizations conditions have been met. However, these indicators are insufficient for rapidly evaluating UV-C room disinfection protocols.

Accordingly, there is a need for a system and method for fast and accurate evaluation of decontamination efficacy. More particularly, there is a need for a system and method for detecting microbial populations on surfaces with high sensitivity and having low detection limits while providing rapid and efficient response to accommodate high turnover. Moreover, the measurement system and methods should be pathogen agnostic, and not be limited by probe-measurand interactions.

SUMMARY OF THE INVENTION

Embodiments of the present invention relate to a system and method for detecting biological material on surfaces after decontamination with UV-C and with high sensitivity and having low detection limits while providing rapid and efficient response to accommodate high turnover. Embodiments of the present invention monitor the disinfection process by detecting changes in the electrical properties of surface-confined biological thin films photodegraded with UV-C radiation using microwaves (MW). MW sensing provides noninvasive, real-time detection of the electromagnetic properties of biological materials via concentrated electromagnetic fields, for which advantages include wide bandwidth, small size, and cost-effective fabrication.

Accordingly, embodiments of the present invention relate to a method of detecting electrical properties of a target biological sample including preparing an analyte film having a predetermined thickness comprising the target biological sample on an electrically non-conductive substrate; providing a ground-signal-ground coplanar waveguide, wherein the coplanar waveguide comprises a transmission medium for a plurality of electromagnetic signals at a predetermined frequency; positioning the substrate comprising the analyte film on the coplanar waveguide to align the transmission medium for the plurality of the electromagnetic signals at the predetermined frequency to pass through the analyte film comprising the target biological sample; irradiating the analyte film comprising the target biological sample with ultraviolet radiation, wherein the irradiating the analyte film comprising the target biological sample comprises denaturing the target biological sample to its molecular components; transmitting the plurality of the electromagnetic signals to the irradiated target biological sample, wherein the plurality of the electromagnetic signals are transmitted through the transmission medium passing through the analyte film comprising the target biological sample, wherein the irradiated target biological sample scatter the plurality of the electromagnetic signals, wherein the scattering of the plurality of the electromagnetic signals comprises reflection, absorption and transmission of the electromagnetic signals; detecting the plurality of the electromagnetic signals scattered by the irradiated target biological sample using a frequency response analyzer; determining a plurality of scattering parameters of the scattered plurality of the electromagnetic signals; and extracting the electrical properties of the target biological sample from the plurality of the scattering parameters. More particularly, the target biological sample comprises double-stranded DNA and the electrical properties of the target biological sample extracted from the plurality of the scattering parameters comprises resistance, inductance, capacitance, and conductance. In some embodiments of the present invention, the method of detecting electrical properties of a target biological sample further includes determining the amount of the irradiated target biological sample from the electrical properties and comparing the determined amount of the irradiated target biological sample to a predetermined threshold value to determine irradiation efficiency.

In one embodiment of the present invention, transmitting the plurality of the electromagnetic signals to the irradiated target biological sample further includes coupling microwaves from an antenna to the target biological sample and applying microwave power to the antenna over a range of frequencies and detecting the plurality of the electromagnetic signals scattered by the irradiated target biological sample comprises determining a frequency response of each of the plurality of the electromagnetic signals scattered by the irradiated target biological sample over a selected frequency range, wherein determining the frequency responses of the plurality of the electromagnetic signals scattered by the irradiated target biological sample further comprises determining resonant peaks in the frequency responses and determining changes in the center frequency or amplitude or both of the resonant peaks.

Embodiments of the present invention also relate to a system for detecting electrical properties of a target biological sample, including a reaction module having a cavity for holding an analyte film comprising the target biological sample; a ground-signal-ground coplanar waveguide having a transmission medium for a plurality of electromagnetic signals at a predetermined frequency range, wherein the coplanar waveguide comprises an input to the transmission medium and an output from the transmission medium, wherein the target biological sample is positioned on the coplanar waveguide such that the plurality of electromagnetic signals pass through the target biological sample along the transmission medium; a first probe antenna mounted on the reaction module in position to transmit the plurality of electromagnetic signals to the analyte film comprising the target biological sample positioned in the cavity of the reaction module, wherein the first probe is coupled to the input to the transmission medium of the coplanar waveguide; a second probe antenna mounted with the reaction module in position to collect at least one of the plurality of the electromagnetic signals scattered by the target biological sample positioned in the cavity of the reaction module, wherein the second probe is coupled to the output to the transmission medium of the coplanar waveguide; and a frequency response analyzer coupled to the first and second probe antennas to provide the plurality of the electromagnetic signals to the first probe antenna and to determine the frequency response of the at least one of the plurality of the scattered electromagnetic signals collected by the second probe antenna and extract the electrical properties of the target biological sample from the scattered electromagnetic signals. More particularly, the reaction module is formed of a material that is transparent to microwave radiation.

In one embodiment of the present invention, the first probe antenna is mounted on an exterior surface of the reaction module with the near field of the first probe antenna coupled to the target biological sample positioned within the reaction module.

In some embodiments of the present invention, the coplanar waveguide further includes a substrate; an first conducting plane deposited on the substrate, the first conducting plane having a first predetermined width, and having a gap of first predetermined length at the midpoint of the conductor; and a second and third conducting planes deposited on the substrate, wherein each of the second and third conducting plane being deposited on one side of the first conducting plane, the spacing between the first conducting plane and each of the second and third conducting plane defining a second predetermined width, wherein the first conducting plane has an anisotropic electric permeability that is different than an electric permeability of the second conducting plane and the third conducting plane, wherein the anisotropic electric permeability of the first conducting plane is selected to be substantially equal to a known permeability component of an electric permeability of the target biological sample, and wherein the second and third conducting planes are ground planes.

In one embodiment of the present invention, further includes an ultraviolet (UV) radiation source. In another embodiment of the present invention, the frequency response analyzer is a vector network analyzer, wherein the frequency response analyzer provides microwave power to the first probe antenna over a range of frequencies from 0.5 GHz to 50 GHz.

In another embodiment of the present invention, the system further includes a signal generator for generating the plurality of the electromagnetic signals at the predetermined frequency range, wherein the signal generator being coupled to the input of the coplanar waveguide through the first probe antenna; and a signal analyzer for analyzing the response of the target biological sample to the plurality of the electromagnetic signals generated by the signal generator, the signal analyzer being coupled to the output of the coplanar waveguide through the second probe antenna.

In an exemplary embodiment of the present invention, the coplanar waveguide is coupled to the signal generator and signal analyzer by means of SMA connectors.

Another embodiment of the present invention relates to a method of detecting electrical properties of a target biological sample, including preparing an analyte film having a predetermined thickness comprising the target biological sample on an electrically non-conductive substrate; providing a ground-signal-ground coplanar waveguide, wherein the coplanar waveguide comprises a transmission medium for microwave signals at a predetermined frequency; positioning the substrate comprising the analyte film on the coplanar waveguide, wherein the transmission medium for the microwave signals pass through the analyte film comprising the target biological sample; irradiating the analyte film comprising the target biological sample with ultraviolet radiation, wherein the irradiating the analyte film comprising the target biological sample comprises denaturing the target biological sample to its molecular components; transmitting the microwave signals to the irradiated target biological sample through the transmission medium passing through the analyte film comprising the target biological sample, wherein transmitting the microwave signals to the irradiated target biological sample further comprises coupling the microwave signals from an antenna to the target biological sample and applying microwave power to the antenna over a range of frequencies, wherein the irradiated target biological sample scatter the microwave signals; detecting a frequency response of each of the microwave signals scattered by the irradiated target biological sample over a selected frequency range; determining resonant peaks in the frequency responses and determining changes in the center frequency or amplitude or both of the resonant peaks; determining a plurality of scattering parameters of the scattered microwave signals; and extracting the electrical properties of the target biological sample from the plurality of the scattering parameters. More particularly, the target biological sample includes double-stranded DNA and the electrical properties of the target biological sample extracted from the plurality of the scattering parameters comprises resistance, inductance, capacitance, and conductance.

In one embodiment of the present invention, the method of detecting electrical properties of a target biological sample further includes determining the amount of the irradiated target biological sample from the electrical properties and comparing the determined amount of the irradiated target biological sample to a predetermined threshold value to determine irradiation efficiency.

DETAILED DESCRIPTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the present invention. Reference will now be made to the drawings wherein like numerals refer to like elements throughout.

Figure 1:
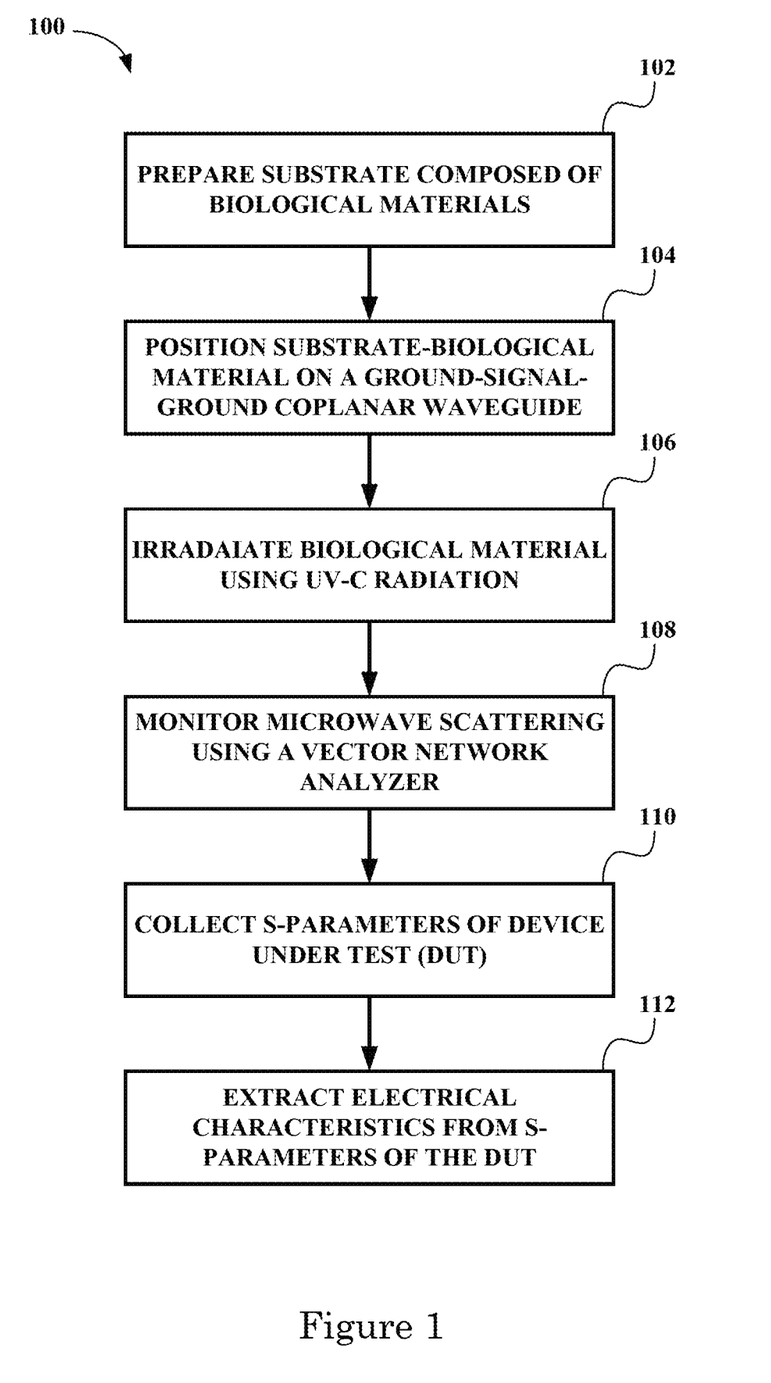
FIG. 1 is a flowchart illustrating an overview of a detection method in accordance with an embodiment of the present invention.

Referring now to the drawings, and more particularly, to FIG. 1, there is shown a method for detecting photoinduced changes in the electrical properties of biological sample, generally designated 100, which comprises embodiments of the present invention.

According to various embodiments, detection method 100 commences by preparing an unpatterned substrate comprised of target analyte at step 102 to create a device under test (DUT). In one embodiment of the present invention, the DUT is a thin film incorporating target biological materials prepared on an electrically non-conductive substrate. Exemplary substrates that can be used in embodiments of the present invention include electrically non-conductive substrates such as paper, glass slide, ceramics, oxidized metal plates (e.g., alumina coated aluminum), and the like. In one embodiment of the present invention, thin film incorporating target biological materials is an optically transparent film. In an exemplary embodiment of the present invention, the DUT is a thin film substrate incorporating deoxyribonucleic acid (DNA) reference prepared by purifying double-stranded DNA (dsDNA) from bacteriophage lambda suspended in a pH 8 Tris Acetate-EDTA buffer (i.e., TE buffer) (500 μg/mL, N3011S, New England Biolabs, Ipswich, MA, USA). Thin films (thickness, n≥3 nm) were generated by spreading 75 μL of the stock across 75% of the area of a glass coverslip (18 mm2, no. 1½, Corning, Corning, NY), which were precleaned with sonication in deionized (DI) water and followed by exposure to oxygen plasma for about 60 seconds. The films were allowed to dehydrate in a biosafety hood for 2 hours and then transferred to a vacuum desiccator for an additional 2 hours of dehydration. The resulting surface densities were 2.8 μg/mm² of DNA for dsDNA films.

Figure 2:
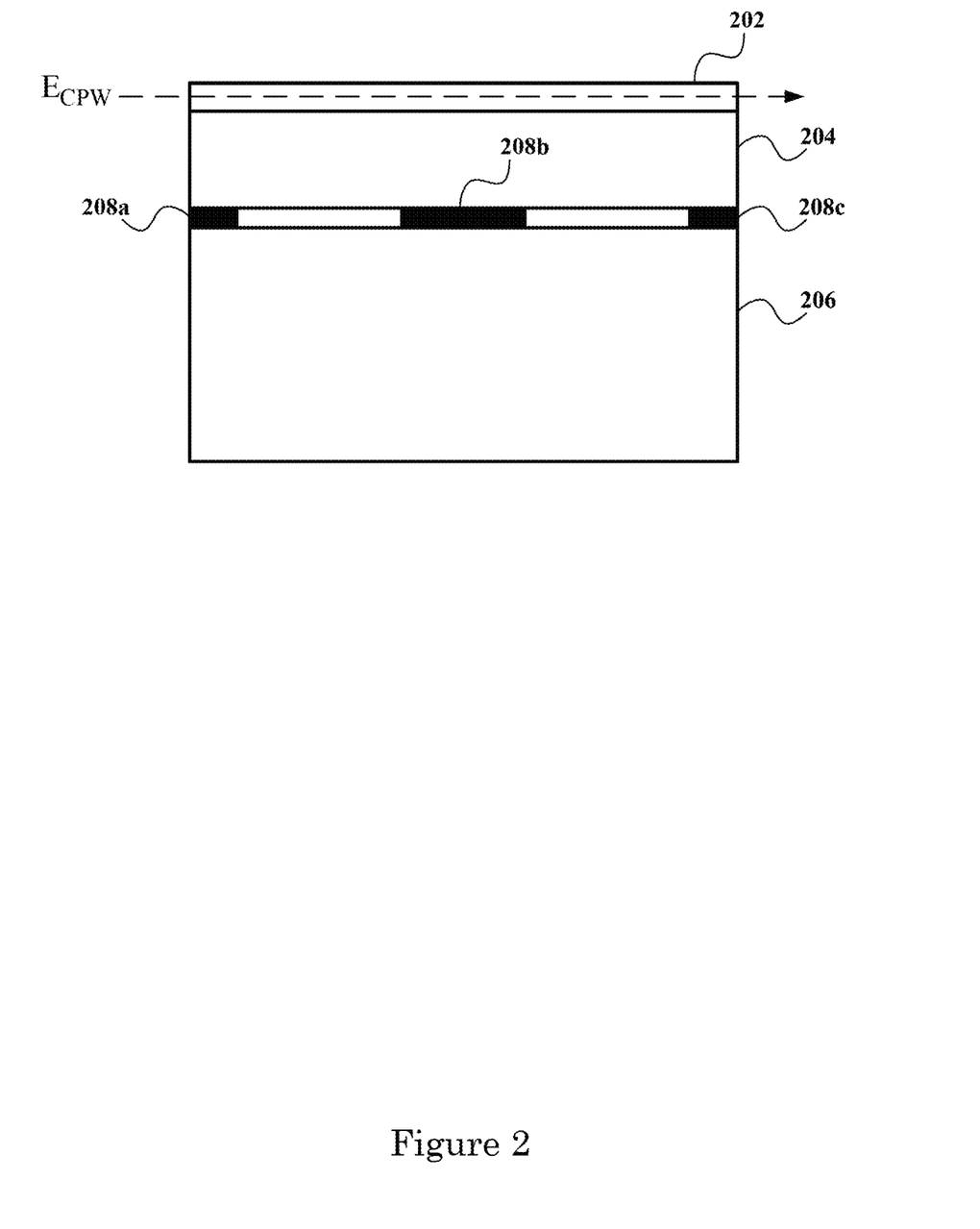
FIG. 2 illustrates an exemplary schematic arrangement of analyte film prepared on a substrate and positioned on a waveguide.

At step 104, unpatterned substrate comprising target analyte prepared at step 102 is positioned on a coplanar waveguide (CPW). CPW includes a transmission medium for an electromagnetic signal at a predetermined frequency, and positioning the unpatterned substrate comprising target analyte on the CPW, provides a transmission medium for the electromagnetic signal to pass through the target analyte. In one embodiment of the present invention, the CPW is a ground-signal-ground CPW (GSG-CPW). FIG. 2 illustrates an exemplary schematic arrangement of analyte film 202 prepared on a substrate 204 and positioned on a waveguide 206. Waveguide 206 includes a conducting plane 208b to carry the MW signal and ground planes 208a and 208c to terminate resultant magnetic fields. The thickness of analyte film 202 is set such that the electric film emanating from waveguide 206 travels through analyte film 202, as illustrated schematically by line $E_{CPW}$ in FIG. 2. In one embodiment of the present invention, thickness of analyte film is about 50 nm, thickness of analyte support is about 1 mm, and thickness of waveguide is about 1.5 mm. In one embodiment of the present invention, the GSG-CPW is a uniform transmission line, and with the sample positioned on it, GSG-CPW can be modeled as a homogenous dielectric filled waveguide, such that a wave propagation constant (Γ) can be defined, as provided in Equation (5) below.

In embodiments of the present invention, a uniform transmission line model is assumed such that the differential equations for the line voltage (V) and current (I) can be expressed in the frequency domain as $$\frac{dV}{dx} = -ZI \tag{1}$$

$$\frac{dI}{dx} = -YV \tag{2}$$

where Z=R+jωL, Y=G+jωC, and R, L, C and G are the line resistance, inductance, capacitance, and dielectric conductance per unit length, respectively. The quantities are normally frequency dependent. A solution to Equations (1) and (2) can be expressed as:

$$V = V_A e^{-\Gamma x} + V_B e^{\Gamma x} \tag{3}$$

$$I = I_A e^{-\Gamma x} + I_B e^{\Gamma x} \tag{4}$$

where, Γ is the propagation constant, and it is defined as $$\Gamma = \sqrt{ZY} = \sqrt{(R+j\omega L)(G+j\omega C)} \tag{5}$$

Electrically, the propagation constant can also be written as
where, $$\alpha = \frac{R}{2\sqrt{L/C}} + \frac{G}{2}\sqrt{\frac{L}{C}} \tag{7}$$

$$\beta = \omega\sqrt{LC} + \left(\frac{R}{2\sqrt{\frac{L}{C}}}\right)\frac{R}{4\omega L} + \left(\frac{G}{2}\sqrt{\frac{L}{C}}\right)\frac{G}{4\omega C} - \frac{RG}{4\omega\sqrt{LC}} \tag{8}$$

The real part of the propagation constant, the attenuation constant (α), can be further resolved into dielectric and conductor losses:

$$\alpha = \alpha_c + \alpha_i \tag{9}$$

where, $$\alpha = \frac{\sqrt{\frac{\omega\mu_0\varepsilon_r}{2\sigma\mu r}}}{n_0 d} \tag{10}$$

-continued $$\alpha = \frac{\omega\sqrt{\mu_r \varepsilon_r \tan\delta}}{2c} \quad (11)$$

And $\mu_0$ is the permeability of free space, $\mu_r$ is the relative permeability, $n_0$ is the characteristic impedance of free space (377Ω), $\varepsilon_r$ is the relative permittivity (i.e., dielectric constant), s is the conductivity of the metal, S is the separation distance between the signal line and its return path (dielectric thickness), c is the speed of light in vacuo, tan δ is the loss tangent of the dielectric—it is the ratio of energy lost to energy stored per cycle, $$\frac{\varepsilon_r''}{\varepsilon_r'} \left( \text{i.e. } \tan\delta = \frac{\varepsilon_r''}{\varepsilon_r'} \right).$$

which signifies the inherent dissipation of electromagnetic energy as the wave propagates in the material.

At step 106, biological material on the substrate positioned on GSG-CPW at step 104 is probed at predetermined intervals with MW while being continuously irradiated with UV-C radiation. In one embodiment of the present invention, biological samples on GSG-CPW are probed every 15 minutes with evanescent MW while being continuously irradiated with UV-C at a dose of 100 µW/cm².

Biomaterials have unique sets of electrical characteristics that are dependent on their dielectric properties and MW-based measurement techniques, such as broadband dielectric spectroscopy (BDS), provide an opportunity to probe and measure dielectric properties as a function of MW frequency. The biomolecules-MW interactions are based on changes in the electric dipole moment of the material in response to changes in an external field (i.e., permittivity). The frequency-dependence of dielectric properties will provide information about the material chemistry. During decontamination of surfaces by exposure to UV-C, the radiation selectively denatures the biological sample to modify its molecular structure by breaking many of the weak linkages, or bonds (e.g., hydrogen bonds), within a molecule that are responsible for the highly ordered structure of the biomolecule in its natural (native) state. In one embodiment of the present invention, during decontamination of surfaces by exposure to UV-C, the radiation selectively denatures the cell's DNA, prevents further reproduction, and leads to a net reduction in observed electrical resistance, which reaches a minimum when almost the entire population is no longer viable. Mechanistically, the observed changes in electrical properties due to UV-C exposure are the result of an eventual disruption in the semipermeable cell membrane, allowing ions and molecules to leak out of the cytoplasm. The loss of cellular integrity is measurable with MW sensors as reduced direct current electrical resistance.

MW are electromagnetic radiation with wavelengths ranging from 1 mm to 1 m in free space and frequencies ranging from 300 MHz to 300 GHz. MW are transmitted, absorbed or reflected depending on the type of material they interact with; the MW-matter interactions are sensitive to both intra- and inter-molecular interactions. MW lose energy when they interact with matter through various mechanisms. The two main microwave loss mechanisms for non-magnetic materials are dielectric (dipolar) and conduction losses. When MW penetrate, and propagate through a dielectric material, the radiation induces polarization within the material that is equal to the dipole moment per unit volume and the internal field generated within the effected volume.

MW also induce translational motions of free or bound species such as electrons, ions, or complexes dipoles. In dielectric materials, MW absorption is maximized through large dielectric repolarization. Analysis of the electromagnetic properties of these dielectric materials, such as complex permittivity and permeability, should provide insights for understanding the underlying mechanism of MW signal losses. In principle, both dielectric properties and electrolytes contribute to the energy loss in biological samples.

As with all electromagnetic radiations, the total MW signal loss involves both dielectric and magnetic loss into the analyte material. While dielectric and electrolytes contribute to the energy loss in biomolecules, the loss tangent must be sufficiently large so that the energy loss into the dielectric far exceeds other loss types and is detectable. Under such conditions, insertion losses can be attributed to energy absorption into the dielectric properties of the analyte and the attenuation constant can be used as a measure of the MW absorption into the cells. For example, the insertion losses in dry thin films of dsDNA can be detected by detecting the changes in the dielectric properties caused by UV-C photodegradation. The attenuation and group velocity (Vg) are related to the group refractive index (ng), and any changes in these parameters give indications of changes in the chemical and electrical properties of the analyte material matrix, especially when new polar functional groups are generated in response to external stimuli. Accordingly, analysis of the electromagnetic properties of materials, such as complex permittivity and permeability, provide insights for an understanding the underlying mechanism of MW signal losses in the analyte, which mechanistically represents the reorientation of electric dipoles. The absorption of MW is related to the material's complex permittivity in the following manner:

$$\varepsilon = \varepsilon_0(\varepsilon' - \varepsilon'') \quad (12)$$

where $\varepsilon_0$ is the permittivity in free space, $\varepsilon'$ is real part of the dielectric constant, and the imaginary part, $\varepsilon''$, is the effective dielectric loss factor.

At step 108, MW scattering are monitored using a frequency response analyzer. In one embodiment of the present invention, the frequency response analyzer is a vector network analyzer (VNA). When MW interact with an analyte, the signals scatter such that a portion of the radiation is reflected backwards toward the source; the remaining signals are partitioned between absorption by the analyte and transmission to the receiver (See FIG. 3). In the case where there is no or minimal net signal absorption as the signals travel through the analyte, the ratio of transmitted to reflected energies (i.e., the extent of scattering) depends in part on the impedance mismatch between the DUT and the source; this is typically about 50Ω for most RF/MW applications. The scattering from the various electrical interfaces is summarized as a matrix that quantifies how RF energy propagates through a multiport network, such as a VNA.

At step 110, MW scattering parameters (S parameters) of the DUT is collected to evaluate the resistance, inductance, capacitance, dielectric conductance per unit length (RLCG) of the analyte, and the attenuation constant respectively, from the microwave insertion loss ($S_{21}$), and use these as metrics to monitor and quantify the changes in the electrical and chemical properties of analyte as a function of the experimental variables.

During the photodegradation process, the biological materials will develop UV-altered species that possess different electrical properties than the pristine material. The total direct current resistance of the sample, calculated from measured S parameters, is a concentration-weighted sum of resistance from the generated UV-altered species, the remaining pristine material, and any UV-inactive species (e.g., ions and trace water). The direct current resistance decreases in proportion to the number of viable cells, due to changes in the cell's composition. When using UV-C for surface decontamination, the UV-C radiation denatures the DNA of cells and prevents further reproduction, leading to a net reduction in observed electrical resistance that reaches a minimum when almost the entire population is no longer viable.

Figure 3:
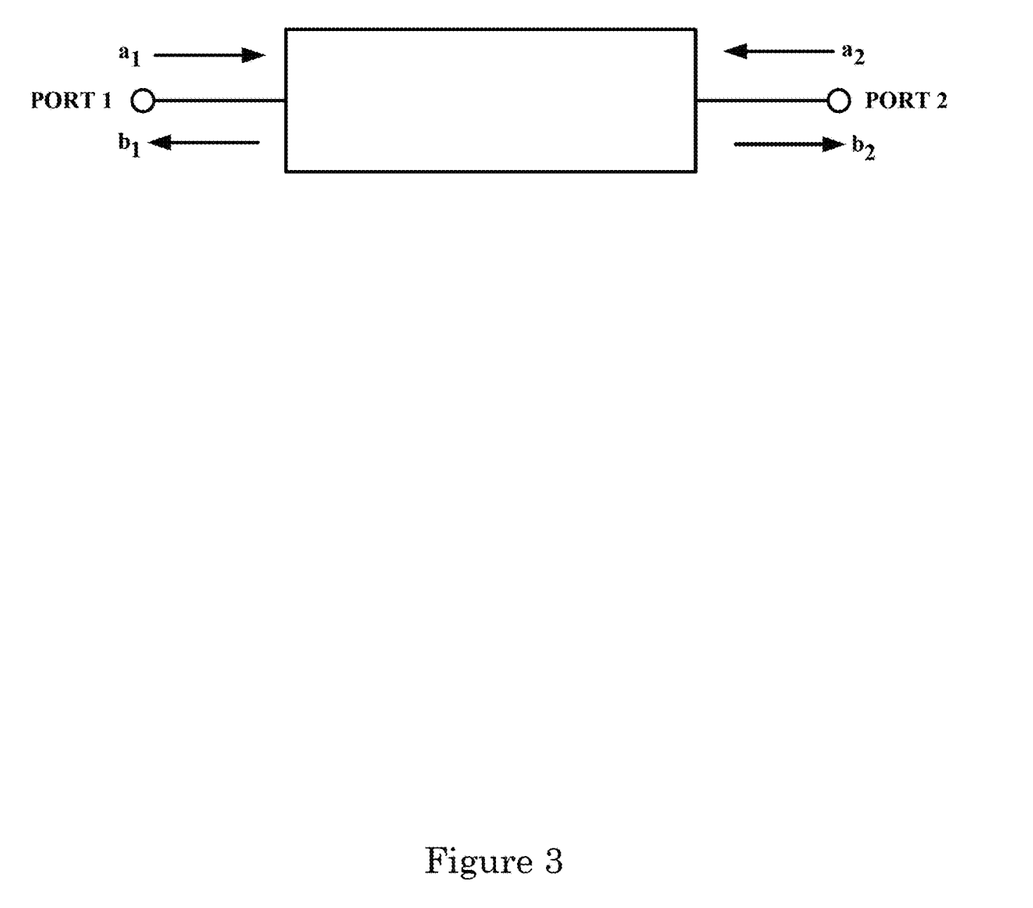
FIG. 3 illustrates an exemplary schematic representation of a two-port Vector Network Analyzer (VNA).

In one embodiment of the present invention, S parameters are measured with a two-port VNA. A typical two-port measurement contains four S parameters ($S_{11}$, $S_{21}$, $S_{12}$, and $S_{22}$) that are vector quantities representing the magnitude and the phase of the frequency-dependent characteristics of the analyte. Identical MW signals emanate from both ports 1 and 2 respectively and travel toward the opposite port. A portion of the incident wave exits through port 1 and is transmitted through the DUT and received at port 2 (dubbed $S_{12}$), with a coefficient $a_2$. A portion of the incident wave is also reflected ($S_{11}$), with a coefficient $b_1$. Similar S parameters, $S_{21}$ and $S_{22}$, are associated with port 2. The portion of the transmitted signal that exits the DUT exits with a different magnitude and phase from the incident signal. Thus, $S_{21}$ and $S_{12}$ also describe the phase difference in degrees between a transmitted signal and an incident signal. The S parameters can be analytically transformed to produce the characteristic circuit element of the analyte.

FIG. 3 illustrates a schematic representation of a two-port VNA, where $a_1$ is the signal into port 1, $b_1$ is the signal out of port 1, $a_2$ is the signal into port 2, and $b_2$ is the signal out of port 2. The S parameters for this conventional element are defined as follows:

$$b_1 = a_1 S_{11} + a_2 S_{12}, \quad (13)$$

and $$b_2 = a_1 S_{21} + a_2 S_{22}, \quad (14)$$

where $S_{11}$ is the port 1 reflection coefficient: $S_{11} = b_1/a_1$, where $a_2 = 0$; $S_{22}$ is the port 2 reflection coefficient: $S_{22} = b_2/a_2$, where $a_1 = 0$; $S_{21}$ is the forward transmission coefficient: $S_{21} = b_2/a_1$, where $a_2 = 0$; and $S_{12}$ is the reverse transmission coefficient: $S_{12} = b_1/a_2$, where $a_1 = 0$. S parameters can be used to evaluate the changes in the analyte's chemo-electrical properties.

Figure 4:
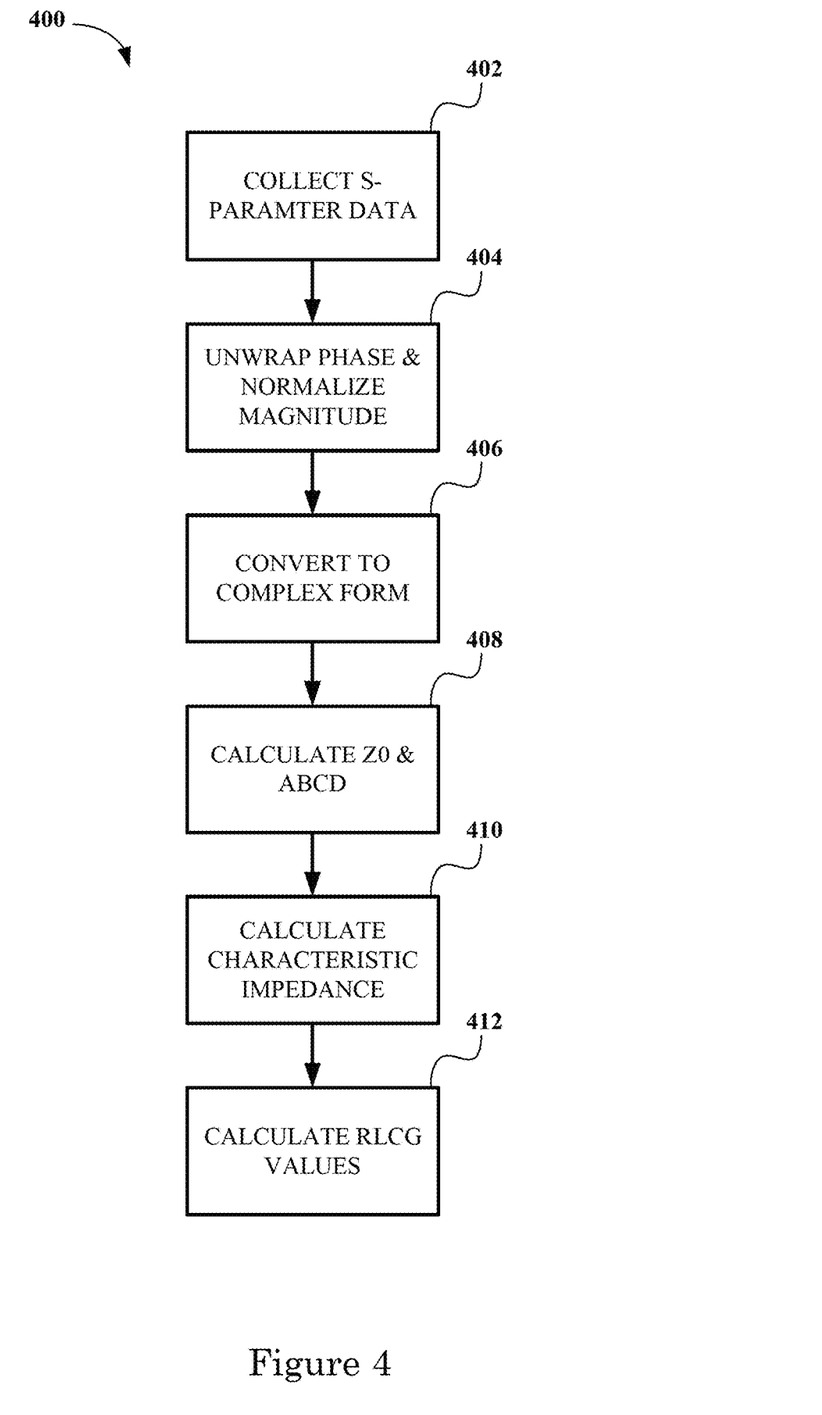
FIG. 4 illustrates an exemplary method for determining electrical data (RLCG values) from MW scattering parameters (S parameters).

At step 112, electrical characteristics is extracted from S parameters of the DUT. In an exemplary embodiment of the present invention, electrical characteristics are extracted from S parameters of the DUT by numerical resistance, inductance, capacitance, and conductance (RLCG) modeling. FIG. 4 illustrates an exemplary protocol 400 for performing a mathematical transformation of MW scattering parameters (S parameters) to electrical data (RLCG values). The electrical data (RLCG values) are compared to a predetermined threshold value to determine the presence of target biological sample. In one embodiment of the present invention, the amount of the irradiated target biological sample is determined from the electrical properties and compared to a predetermined threshold value to determine irradiation efficiency.

Figure 5:
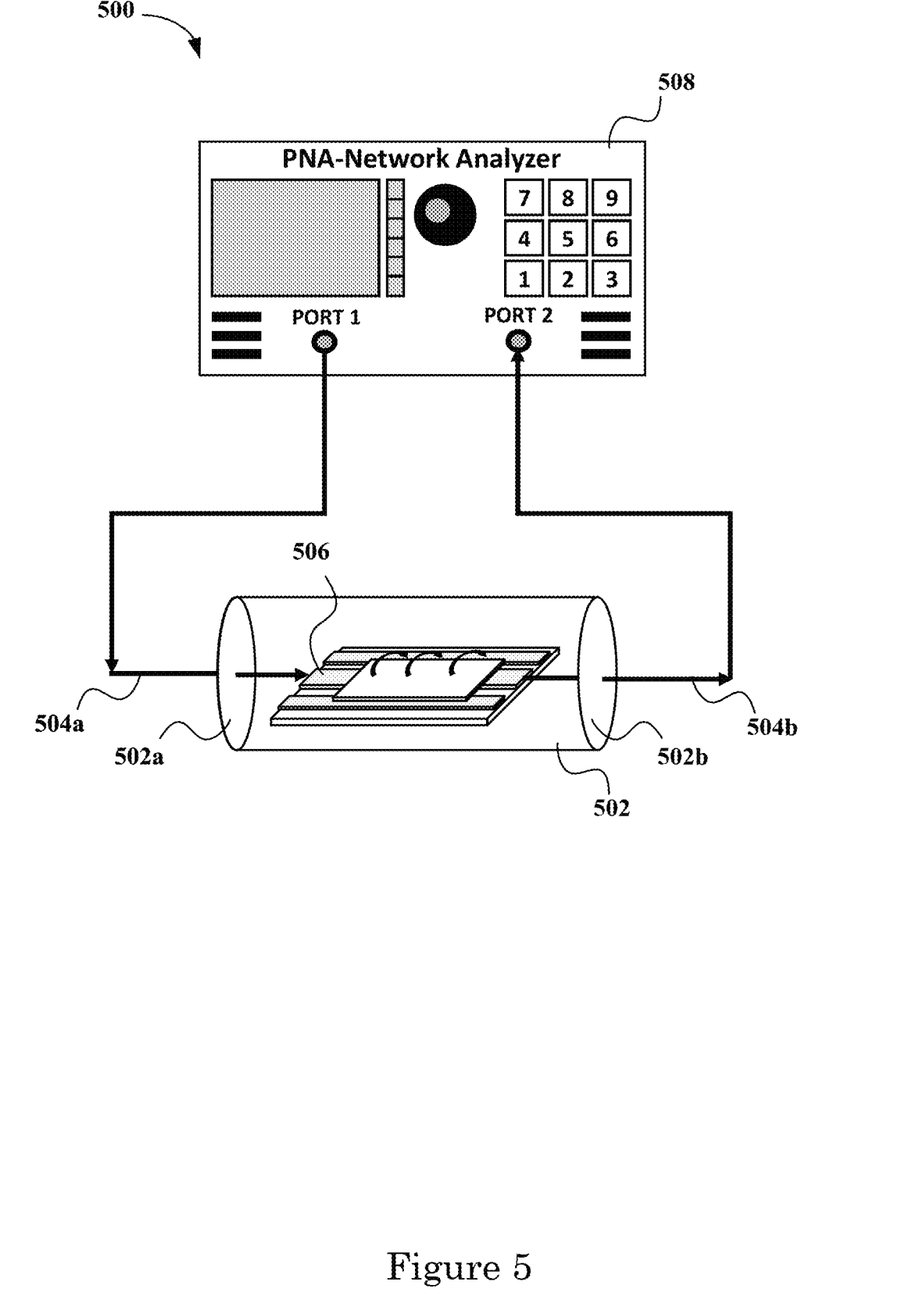
FIG. 5 illustrates a schematic representation of an exemplary system in accordance with embodiments of the present invention for detecting photoinduced changes in the electrical properties of biological sample.

FIG. 5 illustrates schematic representation of an exemplary system 500 for detecting photoinduced changes in the electrical properties of biological sample in accordance with embodiments of the present invention. In one aspect, the system 500 includes a reaction module 502, probe antennas 504a and 504b, a signal path 506, and a frequency response analyzer 508, as shown in FIG. 5, which may be interconnected or networked by way of a communications medium to substantially automate the analysis.

Reaction module 502 includes an interior cavity which is suited to hold a sample therein for analysis. The form of reaction module 502 shown in FIG. 5 is for purposes of illustration only, and reaction module 502 can have other geometric shapes including cylindrical, tubular, rectangular, etc. Sidewall 502a of reaction module 502 is preferably transparent to allow visual inspection of the contents of reaction module 502 and to admit a light beam from a light source to a sample, and an opposite sidewall 502b of reaction module 502 is also preferably transparent so that the light beam can pass through the sample and sidewall 502b. The material forming the walls of sidewall 502b is preferably substantially transparent to microwave electromagnetic energy so that the non-radiated field from probe antennas 504a-b can couple to a sample material within the cavity of reaction module 502. Exemplary materials that may be used to form the walls of reaction module 502 include quartz, fused silica, and the like. In one embodiment of the present invention, the non-radiated field is generally within the near field of probe antennas 504a-b, typically within one wavelength from probe antennas 504a-b.

Probe antenna 504a is mounted, for example, to the exterior surface of a sidewall 502a of reaction module 502 and probe antenna 504b is mounted, for example, to the exterior surface of a sidewall 502b of reaction module 502. Probe antennas 504a-b may also be mounted to an inside surface of a wall of reaction module 502, to top or bottom walls as well as sidewalls 502a-b, or suspended in the cavity of reaction module 502 such that the near field of probe antennas 504a-b is in contact with the sample with probe antennas 504a-b preferably covered to be electrically insulated from the sample. In one embodiment of the present invention, each of probe antennas 504a-b is a resonant slot antenna structure which has a central opening that leaves an open area of the transparent sidewalls 502a-b through which the probe beam can pass. Probe antennas 504a-b may have configurations other than a resonant slot structure. Combined dielectric and optical spectroscopy can also be performed by mounting probe antennas 504a-b at a position where it is out of the light beam, such as on the bottom surface of the container or on a sidewall which is not in the path of the light beam.

Probe antennas 504a-b operate as bioelectrical interface that detects molecular events occurring within the sample using electromagnetic signals. Probe antennas 504a-b include a signal path 506 that is configured to support the propagation of electromagnetic signals over the desired frequency range.

As used herein, the term "signal path" refers to a transmission medium that supports the propagation of an electromagnetic signal at the desired frequency of operation. In one embodiment, the signal path consists of a signal plane/ground plane/dielectric substrate structure capable of supporting a transverse electromagnetic (TEM) signal. Exemplary embodiments of the signal path architecture include coaxial cable, microstrip, stripline, coplanar waveguide, slotline, suspended substrate, and the like. Other exemplary transmission structures include wire, printed circuit board traces, conductive or dielectric waveguide structures, and mutlipolar (e.g., quadrapolar, octapolar) transmission structures. In one embodiment of the present invention, signal path 506 is a GSG-CPW having three conducting planes positioned on a substrate and spaced apart from each other, wherein the center plane is a conductor that acts as the signal (S) plane and the two ground planes (G) positioned to surround the signal (S) plane. In one embodiment, the signal plane has an anisotropic electric permeability that is different from the electric permeability of the ground planes and substantially equal to a known permeability component of an electric permeability of the target biological sample. The ground planes isolate adjacent signals, which effectively reduce the crosstalk commonly encountered when conductive lines are in close proximity to each other. In an exemplary embodiment of the present invention, the signal path architecture includes a GSG-CPW fabricated from a tin-covered printed circuit board (FR4), 61 mm long, with 5 mm wide ground lines separated from the 1.5 mm wide signal line by 1.2 mm gaps. In one embodiment, the signal path includes a single signal port that receives an incident test signal and from which a reflected modulate signal is recovered. In another embodiment, the signal path consists of two or more signal ports: at least one that receives an incident test signal and one that outputs the corresponding modulated test signal.

Probe antenna 504a couples MW to the biological sample positioned within the cavity of reaction module 502 and probe antenna 504b recovers scattered MW after it has interacted with the biological sample positioned within the cavity of reaction module 502. Probe antennas 504a-b are further coupled via a connector, such as a coaxial cable, to a signal source connected to a first port and signal detector connected to a second port of a microwave frequency response analyzer 508, such as commercially available vector network analyzers, reflectometers or spectrum analyzers. When so configured, the signal source and the signal detector can be used to provide a two-port (i.e., a "through") signal response from the sample positioned within the cavity of reaction module 502. The signal source is operable to generate and launch an electromagnetic signal at one or more amplitudes and/or frequencies. The signal detector operates to recover the test signal after it has interacted with (i.e., after electromagnetically coupling to) the sample positioned within the cavity of reaction module 502. In a specific embodiment, the signal source and the signal detector are included within frequency response analyzer 508. In an exemplary embodiment of the present invention, frequency response analyzer 508 provides microwave power to probe antenna 504a over a range of frequencies and measures the response from the sample positioned within the cavity of reaction module 502 via probe antenna 504b coupled to reaction module 502.

In an exemplary embodiment of the present invention, connectors from frequency response analyzer 508 are connected to signal path 506 (e.g., CPW) with edge mount connectors (SMA connectors, Amphenol RF, Danbury, CT). The connectors connecting the CPW can be de-embedded, with a two-port short-open-load-through (SOLT) calibration in which the calibration standards are attached to the end of the feed cables (i.e., the reference plane of the measurement can be moved from the port faces of the VNA to the connector/cable interface) such that the launch connectors and CPW are part of the DUT. In this configuration, the reported S parameters are produced from the inoculated substrates perturbing the electric fields emanating from the signal and terminating on the ground lines in the CPW. Although a broadband range (0.1 GHz to 20 GHz) could be monitored, the reporting frequency of 1.1 GHz may be chosen based on the sample dimensions, the absence of resonances, and minimized signal reflections.

Frequency response analyzer 508 measures the gain and phase response characteristics with respect to frequency of the device under test (also known as DUT) by applying a frequency swept sine wave to it and examining its response signal. Frequency response analyzer 508, essentially comprising a two-port device under test, will exhibit one or more resonant peaks centered at various frequencies. The center frequency or the magnitude (or both) of the peaks will be affected by the permittivity of the sample because of interaction of the non-radiated electromagnetic field from probe antenna 504a and the sample. As this permittivity changes due to the changes in environmental conditions within the cavity of reaction module 502 on the contents of the sample, characteristics of the resonances will change, such as shifts in the center frequencies or changes in the amplitudes of the resonant peaks. In accordance with the invention, the correlation of the changes such as the shift in the center frequencies or changes in amplitudes of the resonant peaks, can be correlated with changes in the environmental conditions applied to the sample to detect the effect of these changes in environmental conditions and to detect changes in characteristics of the sample itself.

Reference now to the specific examples which follow will provide a clearer understanding of system and method in accordance with embodiments of the present invention. The examples should not be construed as a limitation upon the scope of the present invention.

A. Evolution of the Electrical Resistance of Double-Stranded Bacteriophage Lambda DNA During UV-C Exposure.

Figure 6:
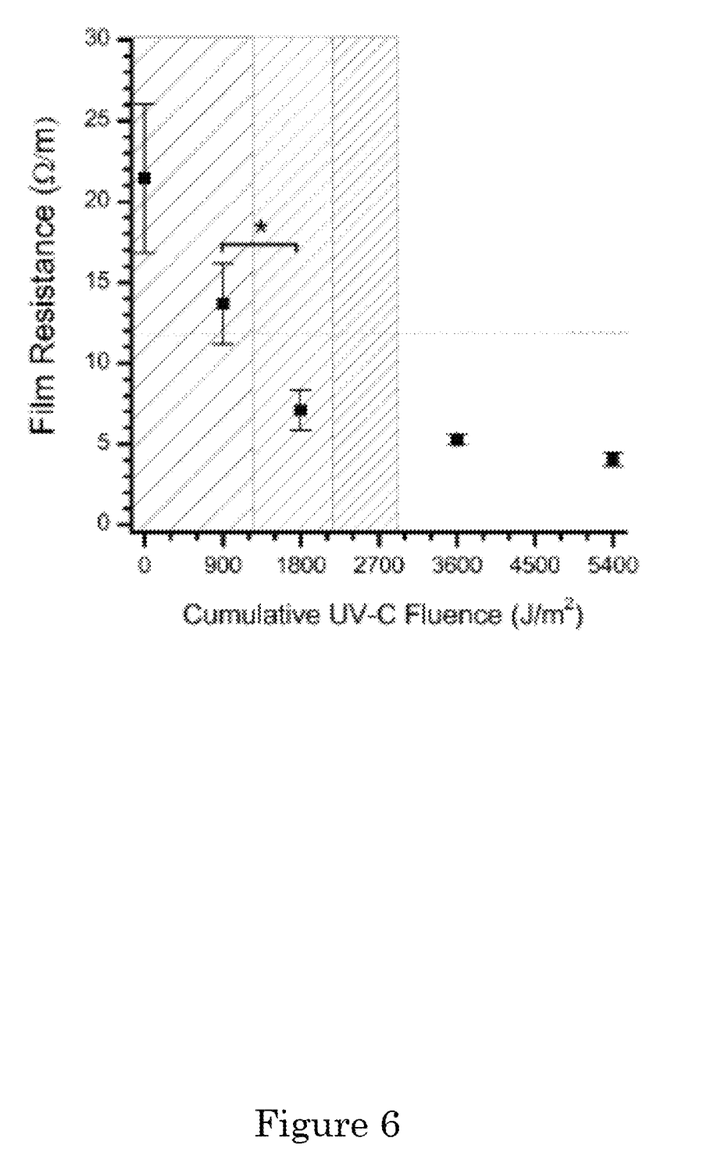
FIG. 6 illustrates an exemplary evolution of the electrical resistance of double-stranded bacteriophage lambda DNA detected using an embodiment in accordance with the present invention.

FIG. 6 shows the evolution of the microwave phase angle ($S_{21}$ monitored at 1.1 GHz) of signal propagation through desiccated double-stranded Bacteriophage lambda DNA thin films on glass during UV photolysis in open air. The error bars represent the standard deviation from a minimum of three replicate samples. The dashed line represents the resistance of the blank substrate. A UV fluence of 900 J/m2 equates to 15 min of UV exposure within our apparatus. The asterisk represents the significant difference between the bracketed points as determined by ANOVA (P value<0.05).

After initial readings, the samples were illuminated with an UV-C lamp (Analytik Jena 95-0016-14 Shortwave UV lamp, 4 W, 115 VAC/60 Hz, Cole-Palmer, Vernon Hills, IL, USA) positioned 5 cm above the outer wall of the quartz reactor (3.8 cm diameter). BDS measurements were performed while dsDNA films were continuously irradiated at a fluence rate of 100 µW/cm$^2$ (measured at the reactor walls). The UV-C radiation fluence experienced by a DUT within the apparatus in accordance with the present invention is 900 J/m$^2$ for every 15 min of UV-C exposure. The electrical resistance was calculated at a frequency of 1.1 GHz. As shown in FIG. 6, the resistance reduces monotonically with UV-C irradiation time to reach a minimum value at which it is presumed there are no or a very few intact DNA-containing cells. Continued UV-C irradiation beyond the minimum electrical resistance point, leads to the photo-induced oxidative decomposition of the organic matter.

B. Evolution of Electrical Resistance Evolution for Naturally Aged and UV-C-Irradiated Desiccated Yogurt Films on Glass Substrate at Room Temperature in Air.

Figure 7:
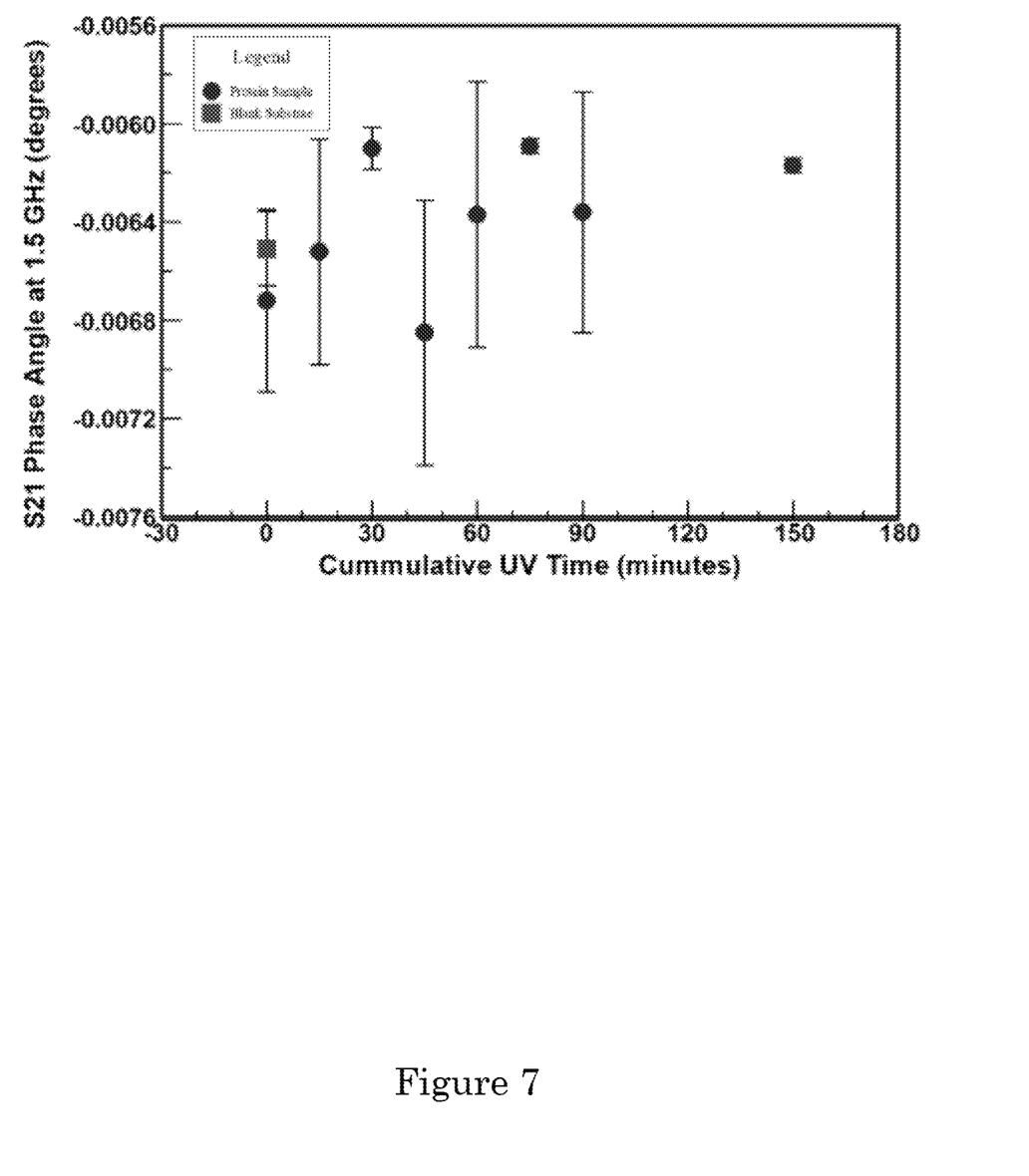
FIG. 7 illustrates an exemplary electrical resistance evolution for naturally aged and UV-C-irradiated desiccated yogurt films on glass substrate at room temperature in air detected using an embodiment in accordance with the present invention.

FIG. 7 shows that the differences in the resistance curve (i.e., 4 hours minimum for the naturally aged compared with the 2 hours minimum for the UV-exposed samples) demonstrate accelerated adding due to UV-degradation, and the capability of the BDS measurement technique to discarnate between live and dead cells irrespective of the analyte composition.

Yogurt provides a useful platform to evaluate the BDS detection of surface cell viability. According to specification, yogurt must contain viable, live, and abundant cultures of the lactic acid bacteria (LAB) *Lactobacillus bulgaricus* and *Streptococcus thermophilus* species at a minimum concentration of $10^7$ CFU/g at the time of manufacture. FIG. 7 compares the electrical resistance of two groups of desiccated yogurt on Corning cover slide samples, one group was exposed to UV-C for 15 minutes and a control group was kept in the dark. In these experiments, while the impact of the desiccation on the viability of microbes in the analytes were not investigated, the following two observations were expected. First, it was expected the UV-C will inhibit the growth of microbes in the exposed samples (UV-aging). Secondly, it was expected the bacteria in the dark will die off when the lactose in the yogurt mixture is depleted since lactose is an important nutrient. The demise of the bacteria manifested as the analyte electrical resistance decreased. Inspection of FIG. 7 shows the electrical resistance of the UV-exposed samples had a minimum at 2 hours, while the control batch had a minimum at 4 hours. This suggests an accelerated demise of the UV-exposed bacteria population from photoinduced DNA damage relative to the control samples that died from starvation. Thus, in principle, the bacterial load in a dairy product could be estimated with proper calibration.

Embodiments of the present invention demonstrate the utility for detecting the viability of surface confined cells. The direct current resistance decreases in proportion to the number of viable cells, due to changes in the cell's composition. When using UV-C for surface decontamination, the UV-C radiation selectively denatures the DNA of cells and prevents further reproduction, leading to a net reduction in observed electrical resistance that reaches a minimum when almost the entire population is no longer viable. This could be a viable technology for meeting diagnostic and decision-making needs. Beyond the minimum resistance point, continued UV-C decomposition leads to photo-induced decomposition of organic matter. It can be concluded that the resistance of the decomposition products may be higher than the that of the dead cells based on recorded observations. In contrast, it has been found that pure protein appears to be insensitive to UV-C exposure beyond outright photo-induced oxidative decomposition, further verifying that the recorded observations indicate embodiments in accordance with the present invention could be used for assessing the efficacy of decontamination of pathogens.

UV irradiation effectively inactivates common pathogens through damage to the genomes by various mechanisms that prevent both transcription and replication. While embodiments in accordance with the present invention focus on HAI-related pathogens, there are other viruses, particularly retroviruses, such as human immunodeficiency virus type-1 (HIV-1) and cancer-causing viruses that could be inactivated by UV-irradiation. RNA damage has been shown to closely mirror the loss of viral infectivity from exposure to germicidal UV irradiation, and that genomic damage is the dominant cause of such pathogen inactivation. As such, embodiments in accordance with the present invention can be used to detect changes in the electrical properties of the compromised genome of the viruses. Embodiments in accordance with the present invention could be further adapted to operate on a very low density of cells, increasing its applicability to more difficult applications where the presence of biological media is expected to be low but hazardous to human health. For example, often infectious agents only need to be present in very minute amounts to cause harm or even death in humans. Being able to apply embodiments in accordance with the present invention to detect and measure the presence of biological cells is advantageous, especially if it can be designed to be portable and small in a hand-held device. It would also be advantageous to pair such metrology with a transportable tunable UV (TTUV) laser system for providing a known irradiance to target surfaces and confined spaces. Embodiments of the present invention can be applied toward the development of a test method and a standard biological test to determine the efficacy of UV-C disinfection. Such a test with biological indicators could be applied to hospital rooms between patient occupancy for a multipoint evaluation to determine whether a room meets a disinfection threshold set for new patients.

Systems and methods for determining detecting photoinduced changes in the electrical properties of a biological sample in accordance with one or more embodiments of the present invention can be adapted to a variety of configurations. It is thought that systems and methods for determining detecting photoinduced changes in the electrical properties of a biological sample in accordance with various embodiments of the present invention and many of its attendant advantages will be understood from the foregoing description and it will be apparent that various changes may be made without departing from the spirit and scope of the invention or sacrificing all of its material advantages, the form hereinbefore described being merely a preferred or exemplary embodiment thereof.

Those familiar with the art will understand that embodiments of the invention may be employed, for various specific purposes, without departing from the essential substance thereof. The description of any one embodiment given above is intended to illustrate an example rather than to limit the invention. This above description is not intended to indicate that any one embodiment is necessarily preferred over any other one for all purposes, or to limit the scope of the invention by describing any such embodiment, which invention scope is intended to be determined by the claims, properly construed, including all subject matter encompassed by the doctrine of equivalents as properly applied to the claims.

What is claimed is:

1. A method of detecting electrical properties of a target biological sample, the method comprising:
   preparing an analyte film having a predetermined thickness comprising the target biological sample on an electrically non-conductive substrate;
   providing a ground-signal-ground coplanar waveguide, wherein the coplanar waveguide comprises a transmission medium for a plurality of electromagnetic signals at a predetermined frequency;
   positioning the substrate comprising the analyte film on the coplanar waveguide to align the transmission medium for the plurality of the electromagnetic signals to pass through the analyte film comprising the target biological sample;
   irradiating the analyte film comprising the target biological sample with ultraviolet radiation, wherein the irradiating the analyte film comprising the target biological sample comprises denaturing the target biological sample to its molecular components;
   transmitting the plurality of the electromagnetic signals to the irradiated target biological sample, wherein the plurality of the electromagnetic signals are transmitted through the transmission medium passing through the analyte film comprising the target biological sample, wherein the irradiated target biological sample scatter the plurality of the electromagnetic signals, wherein the scattering of the plurality of the electromagnetic signals comprises reflection, absorption and transmission of the electromagnetic signals;

detecting the plurality of the electromagnetic signals scattered by the irradiated target biological sample using a frequency response analyzer;

determining a plurality of scattering parameters of the scattered plurality of the electromagnetic signals; and extracting the electrical properties of the target biological sample from the plurality of the scattering parameters.

2. The method of claim 1, wherein transmitting the plurality of the electromagnetic signals to the irradiated target biological sample further comprises coupling microwaves from an antenna to the target biological sample and applying microwave power to the antenna over a range of frequencies.

3. The method of claim 1, wherein detecting the plurality of the electromagnetic signals scattered by the irradiated target biological sample comprises determining a frequency response of each of the plurality of the electromagnetic signals scattered by the irradiated target biological sample over a selected frequency range.

4. The method of claim 3, wherein determining the frequency responses of the plurality of the electromagnetic signals scattered by the irradiated target biological sample further comprises determining resonant peaks in the frequency responses and determining changes in at least one of center frequency and amplitude of the resonant peaks.

5. The method of claim 1, wherein the target biological sample comprises double-stranded DNA.

6. The method of claim 1, wherein the electrical properties of the target biological sample extracted from the plurality of the scattering parameters comprises resistance, inductance, capacitance, and conductance.

7. The method of claim 1, further comprising determining an amount of the irradiated target biological sample from the electrical properties and comparing the determined amount of the irradiated target biological sample to a predetermined threshold value to determine irradiation efficiency.

8. A system for detecting electrical properties of a target biological sample, said system comprising:

a reaction module having a cavity for holding an analyte film comprising the target biological sample;

a ground-signal-ground coplanar waveguide having a transmission medium for a plurality of electromagnetic signals at a predetermined frequency range, wherein the coplanar waveguide comprises an input to the transmission medium and an output from the transmission medium, wherein the target biological sample is positioned on the coplanar waveguide such that the plurality of electromagnetic signals pass through the target biological sample along the transmission medium;

a first probe antenna mounted on the reaction module in position to transmit the plurality of electromagnetic signals to the analyte film comprising the target biological sample positioned in the cavity of the reaction module, wherein the first probe is coupled to the input to the transmission medium of the coplanar waveguide;

a second probe antenna mounted with the reaction module in position to collect at least one of the plurality of the electromagnetic signals scattered by the target biological sample positioned in the cavity of the reaction module, wherein the second probe is coupled to the output to the transmission medium of the coplanar waveguide; and a frequency response analyzer coupled to the first and second probe antennas to provide the plurality of the electromagnetic signals to the first probe antenna and to determine the frequency response of the at least one of the plurality of the scattered electromagnetic signals collected by the second probe antenna and extract the electrical properties of the target biological sample from the scattered electromagnetic signals.

9. The system of claim 8, wherein the reaction module is formed of a material that is transparent to microwave radiation.

10. The system of claim 8, wherein the first probe antenna is mounted on an exterior surface of the reaction module with the near field of the first probe antenna coupled to the target biological sample positioned within the reaction module.

11. The system of claim 8, wherein the coplanar waveguide further comprises:

a substrate;

an first conducting plane deposited on the substrate, the first conducting plane having a first predetermined width, and having a gap of first predetermined length at the midpoint of the conductor; and a second and third conducting planes deposited on the substrate, wherein each of the second and third conducting plane being deposited on one side of the first conducting plane, the spacing between the first conducting plane and each of the second and third conducting plane defining a second predetermined width, wherein the first conducting plane has an anisotropic electric permeability that is different than an electric permeability of the second conducting plane and the third conducting plane, wherein the anisotropic electric permeability of the first conducting plane is selected to be substantially equal to a known permeability component of an electric permeability of the target biological sample, and wherein the second and third conducting planes are ground planes.

12. The system of claim 8, further comprising an ultraviolet (UV) radiation source.

13. The system of claim 8, wherein the frequency response analyzer is a vector network analyzer.

14. The system of claim 8, wherein the frequency response analyzer provides microwave power to the first probe antenna over a range of frequencies from 0.5 GHz to 50 GHz.

15. The system of claim 8, further comprising:

a signal generator for generating the plurality of the electromagnetic signals at the predetermined frequency range, wherein the signal generator being coupled to the input of the coplanar waveguide through the first probe antenna; and a signal analyzer for analyzing the response of the target biological sample to the plurality of the electromagnetic signals generated by the signal generator, the signal analyzer being coupled to the output of the coplanar waveguide through the second probe antenna.

16. The system of claim 15, wherein the coplanar waveguide is coupled to the signal generator and signal analyzer by means of SMA connectors.

17. A method of detecting electrical properties of a target biological sample, the method comprising:

preparing an analyte film having a predetermined thickness comprising the target biological sample on an electrically non-conductive substrate;

providing a ground-signal-ground coplanar waveguide, wherein the coplanar waveguide comprises a transmission medium for microwave signals at a predetermined frequency;

positioning the substrate comprising the analyte film on the coplanar waveguide, wherein the transmission medium for the microwave signals pass through the analyte film comprising the target biological sample;

irradiating the analyte film comprising the target biological sample with ultraviolet radiation, wherein the irradiating the analyte film comprising the target biological sample comprises denaturing the target biological sample to its molecular components;

transmitting the microwave signals to the irradiated target biological sample through the transmission medium passing through the analyte film comprising the target biological sample, wherein transmitting the microwave signals to the irradiated target biological sample further comprises coupling the microwave signals from an antenna to the target biological sample and applying microwave power to the antenna over a range of frequencies, wherein the irradiated target biological sample scatter the microwave signals;

detecting a frequency response of each of the microwave signals scattered by the irradiated target biological sample over a selected frequency range;

determining resonant peaks in the frequency responses and determining changes in at least one of center frequency and amplitude of the resonant peaks;

determining a plurality of scattering parameters of the scattered microwave signals; and extracting the electrical properties of the target biological sample from the plurality of the scattering parameters.

18. The method of claim 17, wherein the target biological sample comprises double-stranded DNA.

19. The method of claim 17, wherein the electrical properties of the target biological sample extracted from the plurality of the scattering parameters comprises resistance, inductance, capacitance, and conductance.

20. The method of claim 17, further comprising determining the amount of the irradiated target biological sample from the electrical properties and comparing the determined amount of the irradiated target biological sample to a predetermined threshold value to determine irradiation efficiency.

* * * * *